United States Patent [19]

Barmentlo et al.

[11] Patent Number: 5,225,049
[45] Date of Patent: Jul. 6, 1993

[54] PROCESS FOR REFINING ORGANIC-SOLVENT CONTAINING CRUDE POLYOL FATTY-ACID POLYESTER PRODUCTS

[75] Inventors: Bart Barmentlo, Delft; Jan Van Buuren, Maasland; Alexander M. Hulstaert, Vlaardingen, all of Netherlands

[73] Assignee: Van den Bergh Foods Co., Division of Conopco, Inc., Lisle, Ill.

[21] Appl. No.: 626,917

[22] Filed: Dec. 13, 1990

[30] Foreign Application Priority Data

Dec. 21, 1989 [EP] European Pat. Off. ........ 89203313.5

[51] Int. Cl.$^5$ .......................... B01D 3/34; C07H 1/06
[52] U.S. Cl. ........................................ 203/34; 203/71; 203/DIG. 6; 203/DIG. 21; 536/119; 536/127; 554/175; 554/176; 554/191
[58] Field of Search ............... 203/34, 6, 71, DIG. 21, 203/DIG. 6; 536/119, 115, 127; 260/419, 420, 424, 428

[56] References Cited

U.S. PATENT DOCUMENTS

| | | | |
|---|---|---|---|
| 3,920,523 | 11/1975 | Lichtenwalter et al. | 203/37 |
| 3,963,699 | 6/1976 | Rizzi et al. | 536/119 |
| 4,334,061 | 6/1982 | Bossier, III | 536/119 |
| 4,480,691 | 11/1984 | Herter et al. | 208/435 |
| 4,517,360 | 5/1985 | Volpenhein | 536/119 |
| 4,518,772 | 5/1985 | Volpenhein | 536/119 |
| 4,797,300 | 1/1989 | Jandacek et al. | 426/601 |
| 4,931,552 | 6/1990 | Gibson et al. | 536/119 |
| 4,942,228 | 7/1990 | Gibson | 536/119 |
| 4,950,140 | 8/1990 | Pflaumer et al. | 426/548 |
| 4,968,791 | 11/1990 | Van Der Plank | 536/119 |
| 5,079,355 | 1/1992 | Grechke et al. | 536/119 |

FOREIGN PATENT DOCUMENTS

| | | | |
|---|---|---|---|
| 0256585 | 2/1988 | European Pat. Off. | |
| 0319091 | 6/1989 | European Pat. Off. | |
| 0319092 | 6/1989 | European Pat. Off. | |
| 0320043 | 6/1989 | European Pat. Off. | |
| 0323670 | 7/1989 | European Pat. Off. | 536/119 |
| 0346845 | 12/1989 | European Pat. Off. | |
| 0349221 | 1/1990 | European Pat. Off. | 536/119 |
| 2161806 | 6/1985 | United Kingdom. | |

*Primary Examiner*—Virginia Manoharan
*Attorney, Agent, or Firm*—Gerard J. McGowan, Jr.

[57] ABSTRACT

A process for refining organic-solvent containing crude polyol fatty-acid polyester reaction product, including the steps of distilling the crude reaction product to substantially remove the organic solvent, and subsequently subjecting the distilled reaction product to a bleaching treatment. The process allows an economic use of bleaching agents while achieving good color and color stability of the refined product.

5 Claims, No Drawings

PROCESS FOR REFINING ORGANIC-SOLVENT CONTAINING CRUDE POLYOL FATTY-ACID POLYESTER PRODUCTS

The present invention relates to a process for refining organic-solvent containing crude polyol fatty-acid polyester reaction products, and in particular, although not exclusively, to such a process for refining crude sugar fatty-acid polyester reaction products.

Polyol fatty-acid polyesters and in particular, the sugar fatty-acid polyesters such as e.g. the sucrose fatty-acid polyesters, are known as suitable low-calorie fat-replacers in edible products. Substantially indigestible for human beings they have physical and organoleptic properties very similar to triglyceride oils and fats conventionally used in edible products. In addition, polyol fatty-acid polyesters are reported to have use as pharmaceutical agents e.g. in view of their ability to take up fat-soluble substances, such as in particular cholesterol, in the gastro-intestinal tract, and subsequently remove these substances from the human body.

In this specification the term "polyol" is intended to include any aliphatic or aromatic compound which comprises at least four free hydroxyl groups. Such polyols in particular include the group of sugar polyols, which comprises the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, maltose, lactose, cellobiose, raffinose, sucrose, erythritol, mannitol, lactitol, sorbitol, xylitol and α-methylglucoside. A generally used sugar polyol is sucrose.

The term "polyol fatty-acid polyester" is intended to include any such polyesters or mixtures thereof of which, on an average, 70% or more of the polyol hydroxyl groups have been esterified with fatty-acids, i.e. which have degrees of esterification of 70% or more.

The term "fatty acid" refers to $C_8$–$C_{24}$ fatty acids which may be saturated or unsaturated, and may have straight or branched alkyl chains.

In general polyol fatty-acid polyesters are synthesized by a process in which a polyol, such as a mono- or disaccharide, is reacted with a fatty-acid lower alkylester, in general the fatty-acid methylester, in the presence of a transesterification catalyst, such as e.g. an alkali metal hydroxide or carbonate, and an emulsifier, such as an alkali metal soap. In a first stage a polyol fatty-acid mono- or oligoester is formed, which in a second stage is further reacted with the fatty-acid lower alkylester to form polyesters of the desired degree of esterification. It is also possible to combine the two stages of the reaction into a single step.

Processes of this type have been described in e.g. the U.S. Pat. Nos. 3,963,699, 4,517,360, and 4,518,772, and EP patent specifications Nos. 0 256 585, 0 301 634 and 0 320 043.

The crude polyol fatty-acid polyester reaction products resulting from conventional syntheses contain in addition to the desired polyesters, components such as fatty-acid soaps, excess fatty-acid lower alkylesters and polyol fatty-acid oligoesters. Also, due to the relatively high temperatures at which conventional processes are carried out, often by-products are formed which may be undesirable in view of their chemical characteristics, such as in particular discoloring properties. In general it is therefore necessary to further purify or refine the crude polyol fatty-acid polyester reaction products resulting from such conventional syntheses.

The term "crude polyol fatty-acid polyester reaction product" is intended to refer to unrefined or partially refined reaction products of processes for the synthesis of polyol fatty-acid polyesters. The two volume-wise major components in such crude compositions in general are the polyol fatty-acid polyester component and the organic solvent.

For the purposes of the present specification the term 'organic solvent' is intended to refer to the group of relatively volatile fatty-acid sources as may be used in excess amount in the synthesis reaction of the polyol fatty-acid polyester, and any organic solvents used or introduced during synthesis or refining.

A prominent example of such a relatively volatile fatty-acid source is e.g. fatty-acid lower alkylester used in the transesterification reaction described hereinbefore.

In the crude reaction product the polyol fatty-acid polyester component is generally present in an amount of 10 to 95% by weight of the crude product, and the organic solvent is generally present in an amount of 5 to 90% by weight.

Conventional refining methods comprise a variety of different treatments including washings with water, organic solvents, acid or alkaline solutions, salting-out treatments, bleaching steps, distillation, stripping and deodorisation treatments.

In general the washing treatments aim at a substantial reduction of the soap component which can be present in the crude polyol fatty-acid polyester reaction product by reason of its use as the emulsifier system in the preceding synthesis reaction of the polyester or, to a limited extent, due to partial conversion to soap of the fatty-acid source, such as the fatty-acid lower alkylester.

These washing treatments are often followed by a bleaching treatment with adsorbents such as bleaching earth, activated carbon and silicas, primarily aimed at removing colored matter, discoloring materials, residual soap and metal ions. Descriptions thereof can be found in U.S. Pat. No. 4,334,061, EP 0 319 091 and EP 0 319 092.

Adsorbents are well-known in conventional oil technology. Although very suitable and to some extent indispensible for the purpose of their use, large volume use thereof is uneconomical in view of the costs associated with the adsorbents themselves, reductions in oil yield, and the disposal of spent adsorbents.

It is therefore a first object of the present invention to provide a bleaching treatment suitable for the refining of crude polyol fatty-acid polyester reaction products which allows a reduced level, or alternatively a more effective use, of the adsorbent used in the bleaching treatment.

It is a further object of the present invention to provide a bleaching treatment by which low color characteristics and low levels of discoloring components are achieved and the discoloring problems during subsequent refining steps are avoided.

Accordingly, in its broadest aspects the present invention provides a process for refining organic-solvent containing crude polyol fatty-acid polyester reaction product, comprising the steps of:
(a) distilling the crude reaction product to substantially remove said organic solvent; and (b) subsequently subjecting the distilled reaction product to a bleaching treatment.

The key feature of the present invention is that the distilling step by which the organic solvent and optionally further volatile components present in the crude reaction product are removed to a substantial degree, takes place before the bleaching treatment to remove colored matters.

Accordingly, in the refining process according to the invention a substantial part of the organic solvent is removed by distillation before a further bleaching treatment. Also further volatile components such as e.g. free fatty acids may be removed in the distilling step.

The distillation of the crude reaction product may be carried out in conventional manner using temperatures in the range of from 60° to 300° C. In general temperatures of above 150° C. will be used since these allow reduced pressure regimes economically feasible on a technical scale. Preferred distilling temperatures lie within the range of 160° to 240° C., temperatures of 200° to 240° C. being preferred most.

As already indicated the distilling step is preferably carried out under reduced pressure, in particular pressures of below 100 mbar, such as between 30 and 70 mbar. Pressures of between 1 and 10 mbar and in particular pressures between 1 and 5 mbar are preferred.

Although appropriate distilling times will strongly depend upon temperature and pressure conditions applied, e.g. batch-wise distilling times of between 30 and 100 minutes have been found suitable, whereas continuous distilling times can be much shorter and are determined by the equipment used.

In exceptional circumstances where the crude reaction product at the distilling stage still comprises significant levels of relatively temperature-sensitive components it may be necessary to use relatively low distilling temperatures within the range of 60° to 150° C., in particular, 80° to 120° C. Removal from or reduction in the crude reaction product of the relevant organic components by distilling at such low temperatures will require more severe reduced pressure conditions, in particular, of below 1 mbar, or even below 0.1 mbar.

Although technically best results are achieved when the organic solvent is substantially removed from the crude reaction product prior to a subsequent bleaching treatment, worthwhile advantages are already obtained at removal levels of 40% or more by weight of the organic solvent, removal levels of 70% or more being preferred, and levels of 95% or more being preferred most.

A further essential element of the present invention is the bleaching treatment subsequent to the distilling of the reaction product. The bleaching treatment and the bleaching agent selected is particularly triggered towards effective removal of the colored matter. Suitable bleaching agents are carbons and bleaching earths, which may or may not be activated by appropriate acid treatment, silicas, clays and synthetic adsorbents.

Suitably, the bleaching agents are added to the reaction product in amounts of 0.2 to 5% by weight and preferably in amounts of 0.5 to 3% by weight. Often very good results are obtained with amounts of 1 to 2% by weight.

In general the bleaching treatment is carried out at an elevated temperature. Suitable bleaching temperatures are within the range of 70° to 140° C., temperatures of 80° to 120° C. being preferred.

Dependent upon the bleaching agent selected bleaching results may be improved by the presence in the reaction product of low levels of water. In particular when silicas are used water levels are best between 0.1 and 0.5%. Where bleaching is best carried out under dry conditions, such as e.g. when bleaching earths are used, suitably conditions of reduced pressure are applied, pressures of below 100 mbar and in particular between 30 and 70 mbar being preferred.

Normal bleaching times vary between 30 and 120 minutes, times of between 30 and 60 minutes in many instances being sufficient.

After the bleaching treatment the bleaching agent together with the absorbed colored materials are in general removed by filtration which may be assisted by introduction of a filter aid such as cellulose.

In addition to the distilling and subsequent bleaching treatment the refining process in accordance with the present invention preferably comprises refining treatments preceding the distilling step to substantially remove the soap and metal ion components in the crude reaction product. Removal of these components will avoid problems of discoloring during subsequent high-temperature refining treatments, such as the distilling step. At the stage before the distilling step it is not so much an object to remove the colored matter and this may suitably be primarily effected during the bleaching step subsequent to the distilling.

These pre-distilling treatments may comprise any suitable method to substantially remove in particular the soap and alkali metal ions which may be present in the crude reaction product. Suitable such refining treatments include conventional washing treatments such as water washings with or without added electrolytes, and alkaline or acid washings as described in EP 0 319 092 herein incorporated by reference.

Instead of or in addition to such conventional washing treatments preceding the distillation it may be especially useful to contact the crude polyester reaction product with an acid to substantially convert the soap component to its corresponding free fatty acids.

The acid is used to establish conversion of the soap component to its free fatty acids and the amount thereof in principle must be sufficient to substantially convert all of the soap present in the crude polyester product. The amount of acid will depend upon the level of the soap emulsifier system used in the synthesis reaction as well as the amounts of soap formed or introduced during the synthesis reaction. For reasons of cost it is preferred that the amount of acid is as close to the precise amount needed as technically feasible to establish full neutralising of all the soap present in the crude reaction product, amounts of acid in excess over what is theoretically needed to fully neutralize the alkaline components in the crude polyester reaction product preferably being as low as 0 to 10%, the range of 0 to 5% being particularly preferred.

To ensure substantially full conversion of the soap to free fatty acids the strength of the acid must be such that the equilibrium of the conversion reaction lies substantially fully at the side of the free fatty acids, the pH-values resulting from the addition of the acid to the crude reaction product, in general in the form of an aqueous solution thereof, preferably being below 6, the range of pH 3 to 5 being preferred most.

Suitably, both inorganic and organic acids can be used which in view of the important application of the polyol fatty-acid polyesters in food products preferably are food grade. Suitable inorganic acids are phosphoric acid and dihydrogen phosphoric acid alkali metal salts. Suitable organic acids include acetic, lactic, succinic and citric acid, the latter acid being preferred.

Preferably, a relatively concentrated aqueous acid solution is used. Suitable concentrations lie within the range of 25% by weight or more. To allow convenient removal of the salt resulting from the acid step, concentrated acid solutions of 40% to 85% are preferred, concentrations of 40 to 60% being preferred most.

The acid step has to be followed by substantial removal from the crude polyester reaction product of any salts present therein, in general alkali-metal salts which together with the free fatty acids result from the soap conversion by the acid. The substantial removal of the salt may be effected by using conventional separation techniques, such as centrifuge or filtration techniques. Suitable filtration techniques may involve the use of filter-aids, such as e.g. cellulose.

In particular, when the salt is removed by way of filtration, it has been found that the removal of this salt, generally being the alkali metal salt of the acid used in the soap-conversion step, is improved if the water level in the acidulated reaction product resulting e.g. from the aqueous acid solution, is reduced to very low levels which preferably correspond to a system substantially without free water being present, i.e. all water being either dissolved in the polyester phase or being present as crystal or bound water of further components in the reaction product. Suitable such water levels are below 0.3% by weight, and preferably lie below 0.1 or even 0.05% by weight. This can be conveniently effected by subjecting the reaction product to appropriate drying conditions at elevated temperature and reduced pressure. This drying step may be carried out subsequent to or during the contact times discussed herein-before.

A preferred method of reducing the water to very low levels is flash-drying by which the reaction product is passed into a low-pressure chamber and any water present is vaporised adiabatically. The heat needed for such evaporation is drawn from the reaction mixture and accordingly this method can be used for the simultaneous drying and cooling of the reaction mixture from the temperature of the acid step to well below 100° C., in particular 70° to 90° C. If flash-drying is used for simultaneous drying and cooling, the water level in the reaction mixture after the addition of the acid solution may be higher than described hereabove, in order to ensure sufficient cooling during the flash-drying process. Water levels of 2 to 5% by weight will ensure a cooling of about 20° to 50° C. which in general will avoid any further separate cooling step.

It has further been found that the removal of the salt as also the color and discoloring properties of the final refined polyester product are advantageously effected, if prior to the introduction of the acid in the pre-distilling treatment first a relatively small amount of an aqueous alkaline solution is added to the crude polyester product which is subsequently neutralized by the acid simultaneous to the conversion of the soap component to its free fatty acid.

Within the constraint of avoiding or minimizing the risk of the formation of undesirable components the particular combination of source, volume and level of alkalinity is not very critical and can be any of the readily available alkaline materials, such as the alkali metal hydroxides, carbonates or silicates, generally at a level within the range of 0.1 to 6N, in particular, 0.2 to 4N, or even, 0.2 to 1 or 2.5N. The aqueous alkaline solution is suitably added to the crude polyester product in an amount of 0.5 to 5% by weight of the product. Preferably, some agitation is applied to improve the contact between the crude polyester product and the aqueous alkaline solution.

In a batch-wise operation contact times in the acid step and optional prior alkaline step of between 1 and 10 minutes between the introduction of the aqueous alkaline solution and the introduction of the acid have been found sufficient. In a continuous operation contact times are generally shorter than 3 minutes, such as less than about 1 minute, and can be as short as 5 to 30 seconds.

Although in the pre-distilling refining treatment the acid step and optional prior alkaline step can be combined with further conventional washings as described hereinbefore, it is preferred to apply the acid step and the optional prior addition of an aqueous alkaline solution without further washing steps.

A preferred pre-distilling treatment to substantially remove any soap and alkali metal ion components may further consist of a bleaching treatment which contrary to the bleaching treatment subsequent to the distilling step is not so much directed to removal of colored matter but directed to the removal of residual soap and alkali metal ions. The process may then comprise a process for refining organic solvent-containing crude polyol fatty acid polyester reaction product comprising the steps of (a) prior to step (b) substantially removing the soap and metal ion components in the crude reaction product including a bleaching treatment, (b) distilling the crude reaction product resulting from step (a) to substantially remove the organic solvent and (c) subjecting the distilled reaction product resulting from step (b) to a bleaching treatment to remove colored matter.

Suitably, similar adsorbent agents and bleaching conditions can be used as described hereinbefore.

Accordingly, in a preferred embodiment of the present invention the refining process comprises subjecting the crude reaction product to a first bleaching treatment, subsequently distilling the once bleached reaction product to substantially remove the organic solvent; and subjecting the distilled reaction product to a second bleaching treatment.

In a particularly preferred embodiment the present invention provides a refining process in which before the distilling step the crude reaction product is contacted with an acid followed by removal of salt as described hereinbefore, and subjected to a first bleaching treatment, the absorbent of said first bleaching treatment being introduced before said removal of salt. In such a process the removal of salt and adsorbent is suitably be combined.

Subsequent to the second bleaching treatment the resulting polyester product may be subjected to a high-temperature refining treatment to remove volatile components and any residual free fatty acids. Such high-temperature refining treatment in particular will include a further deodorizing step, such as steam-stripping, at a temperature of above 150° C., such as 150° to 300° C. Preferred temperatures are 180° to 260° C., in particular 190° to 240° C., temperatures of 220° to 240° C. being preferred most.

The invention is in particular directed to the refining of crude polyol fatty-acid polyester reaction products of transesterification reactions involving excess amounts of fatty-acid lower alkylesters. This type of transesterification reaction is particularly suitable for the synthesis of polyol fatty-acid polyesters having high degrees of esterification of 70% or more, and accordingly, the present process is particularly applicable to the refining of crude polyol fatty-acid polyester having such high degrees of esterification, in particular crude products comprising polyol fatty-acid polyesters having degrees of esterification of 80% or more, or even 90% or more. Preferably, such crude polyester reaction products derived from the sugar polyols selected from the group of disaccharides or the alcohol derivatives thereof, such as sucrose, and esterified to over 95% fatty-acid substitution, are suitably refined by the process in accordance with the present invention.

Having a reduced risk of discoloring the polyol fatty-acid polyesters refined in accordance with the process of the present invention are particularly suitable to replace fully or partially conventional triglyceride fats in food compositions intended for high-temperature purposes, such as baking and frying oils. Generally, in such food compositions at least 10% by weight of the conventional triglyceride fat is replaced by the polyol fatty-acid polyesters in accordance with the present invention. Preferably, at least 50% of the conventional fat is replaced by the polyesters.

The invention is now further illustrated with reference to the following examples, percentages being by weight unless indicated otherwise.

EXAMPLE 1

A batch of crude sucrose fatty-acid polyester reaction product, synthesized in a solvent-free transesterification reaction between sucrose and touch-hardened soybean oil derived, non-distilled fatty-acid methylester to a degree of esterification of over 95%, consisted of the following components:

| | |
|---|---|
| sucrose fatty-acid polyester | 44.6% |
| fatty-acid methylester | 46.9% |
| soap (mainly coconut-derived potassium soap) | 3.8% |
| minor components | 4.7% |

This batch was first washed with 7.5% of water, agitated during 15 minutes at 80° C. and centrifuged (3000 rpm for 10 minutes) to separate the water with the bulk of the soap and dried at 90° C. and 50 mbar pressure. The water-washed sucrose polyester reaction product was further refined using 3 different procedures:

procedure 1

20 grams bleaching earth (Supreme FF ex Tonsil ®) was added per kg water-washed sucrose polyester reaction product and the resulting mixture was stirred for 30 min at 90° C. and atmospheric pressure. The suspension was filtered through a 2 microns filter and distilled/-deodorised (3 hours, 200° C.)

The color values of the refined reaction product as measured in a 2" cell of an Automatic Colori Meter ex Morgan Smith Electronics Ltd ® were 24.0 Yellow and 3.4 Red.

procedure 2

10 grams bleaching earth (Supreme FF ex Tonsil ®) was added per kg water-washed sucrose polyester reaction product and the resulting mixture was stirred for 30 min at 90° C. and atmospheric pressure. The suspension was filtered through a 2 microns filter and distilled (1 hour, 200° C.) to remove the bulk of the fatty-acid methylester (>95% removal). After distillation the reaction product was dried (50 mbar, 90° C.) and 10 grams bleaching earth (Supreme FF ex Tonsil ®) was added per kg distilled reaction product. The suspension was stirred for 30 min (atmospheric, 90° C.) and filtered through a 2 microns filter, followed by deodorisation at 200° C. for 2 hours.

The color values of the refined reaction product as measured in a 2" cell of an Automatic Colori Meter ex Morgan Smith Electronics Ltd ® were 19.0 Yellow and 2.5 Red.

procedure 3

10 grams bleaching earth (Supreme FF ex Tonsil ®) per kg water-washed sucrose polyester reaction product was added and the resulting mixture was stirred for 30 min at 90° C. and atmospheric pressure. The suspension was filtered through a 2 microns filter. The reactant product was subsequently dried (50 mbar, 90° C.) and the bleaching treatment repeated. Subsequently, the twice bleached product was distilled/deodorised at 200° C. for 3 hours.

The color values of the refined reaction product as measured in a 2" cell of an Automatic Colori Meter ex Morgan Smith Electronics Ltd ® were 25.0 Yellow and 3.2 Red.

Comparison of the color results after the 3 different procedures indicate that procedure 2, which embodies the process of the present invention, is the most effective having the best color results while requiring less bleaching earth than the procedures 1 and 3 (15 grams compared to 20 grams per kg crude reaction product).

EXAMPLE 2

A batch of crude sucrose fatty-acid polyester reaction product, synthesized in a solvent-free transesterification reaction between sucrose and touch-hardened soybean oil derived, distilled fatty-acid methylester to a degree of esterification of over 95%, consisted of the following components:

| | |
|---|---|
| sucrose fatty-acid polyester | 49.8% |
| fatty-acid methylester | 43.2% |
| soap (mainly coconut-derived potassium soap) | 3.8% |
| minor components | 3.2% |

This batch was first washed with 7.5% of water, agitated during 15 minutes at 80° C. and centrifuged at 3000 rpm for 10 minutes to separate the water with the bulk of the soap and dried at 90° C. and 50 mbar pressure. After drying 0.2% by weight of water was added. Subsequently, after 5 minutes stirring 0.5% of Trisyl ex Grace ® was added to remove residual soap and the resulting mixture was stirred for 30 min at 90° C. and atmospheric pressure and filtered through a 2 microns filter.

The resulting product was further refined using two different procedures.

procedure 1

15 grams of bleaching earth (Standard FF ex Tonsil ®) was added per kg of partially refined sucrose polyester reaction product and the resulting mixture was stirred for 30 min at 90° C. and atmospheric pressure. The suspension was filtered through a 2 microns filter and distilled/deodorizes (3 hours, 215° C.).

The color values of the refined reaction product as measured in a 2" cell of an Automatic Colori Meter ex Morgan Smith Electronics Ltd ® were 30.0 Yellow and 3.7 Red.

procedure 2

The partially refined sucrose polyester reaction product was first distilled (1 hour, 215° C.) to remove the bulk of the fatty-acid methylester (>95% removal). After distillation the reaction product was dried (50 mbar, 90° C.) and 15 grams of bleaching earth (Standard FF ex Tonsil ®) was added per kg distilled reaction product. The suspension was stirred for 30 min (atmospheric, 90° C.) and filtered through a 2 microns filter, followed by deodorization at 215° C. for 2 hours.

The color values of the refined reaction product as measured in a 2" cell of an Automatic Colori Meter ex Morgan Smith Electronics Ltd ® were 29.0 Yellow and 3.7 Red.

Comparison of the 2 procedures shows that procedure 2 in accordance with the invention gives equal or even somewhat better color results but requires less bleaching earth to achieve this (15 grams per kg distilled product compared to 15 grams of non-distilled product which amounts to about 67%).

We claim:

1. A process for refining a crude polyol fatty acid polyester reaction product obtained by transesterification of a polyol and a fatty acid lower alkyl ester in the presence of a fatty acid soap emulsifier including alkali metal ions and a transesterification catalyst, comprising the steps of:
    (a) prior to step (b) substantially removing alkali metal ions of said emulsifier and said transesterification catalyst from said crude reaction product including subjecting the crude reaction product to a bleaching step for removal of residual alkali metal ions;
    (b) distilling said crude reaction product resulting from step (a) to substantially remove organic solvent consisting essentially of said fatty acid lower alkyl ester; and
    (c) subjecting the distilled reaction product resulting from step (b) to a bleaching treatment for removal of colored matter.

2. The process of claim 1 in which step (b) is carried out at a temperature within the range of 200° to 240° C.

3. The process of claim 1 in which in step (b) 70% or more of said organic solvent is removed.

4. The process of claim 1 which subsequent to step (c) comprises further refining treatments at a temperature of 180° to 260° C.

5. The process of claim 1, where step (a) further comprises contacting the crude reaction product with an acid to convert said fatty acid soap emulsifier to its corresponding free fatty acid and alkali metal salt.

* * * * *